US009937341B2

(12) United States Patent
Pianca et al.

(10) Patent No.: US 9,937,341 B2
(45) Date of Patent: Apr. 10, 2018

(54) LEADS WITH NON-CIRCULAR-SHAPED DISTAL ENDS FOR BRAIN STIMULATION SYSTEMS AND METHODS OF MAKING AND USING

(71) Applicant: BOSTON SCIENTIFIC NEUROMODULATION CORPORATION, Valencia, CA (US)

(72) Inventors: Anne M. Pianca, Santa Monica, CA (US); Courtney C. Lane, Ventura, CA (US); James C. Makous, N. Potomac, MD (US); Andrew DiGiore, San Francisco, CA (US); Ellis Garai, Stanford, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 9 days.

(21) Appl. No.: 14/622,144

(22) Filed: Feb. 13, 2015

(65) Prior Publication Data
US 2015/0151111 A1 Jun. 4, 2015

Related U.S. Application Data

(63) Continuation of application No. 12/237,888, filed on Sep. 25, 2008, now abandoned.

(51) Int. Cl.
*A61N 1/00* (2006.01)
*A61N 1/05* (2006.01)
(Continued)

(52) U.S. Cl.
CPC ......... *A61N 1/0534* (2013.01); *A61N 1/0529* (2013.01); *A61N 1/0472* (2013.01); *A61N 1/36082* (2013.01)

(58) Field of Classification Search
CPC .................................................. A61N 1/0472
See application file for complete search history.

(56) References Cited

U.S. PATENT DOCUMENTS

| 4,112,953 A | 9/1978 | Shanker et al. |
| 4,577,643 A | 3/1986 | Beranek |

(Continued)

FOREIGN PATENT DOCUMENTS

| EP | 879016 | 10/2003 |
| EP | 1935448 | 6/2008 |

(Continued)

OTHER PUBLICATIONS

Official Communication for U.S. Appl. No. 12/237,888 dated Dec. 8, 2011.

(Continued)

*Primary Examiner* — Michael Carey
*Assistant Examiner* — Elizabeth K So
(74) *Attorney, Agent, or Firm* — Lowe Graham Jones PLLC; Bruce E. Black

(57) ABSTRACT

A lead is configured and arranged for brain stimulation. The lead includes a proximal end and a distal end. The proximal end includes a plurality of terminals disposed at the proximal end. The distal end has a non-circular transverse cross-sectional shape and includes a plurality of electrodes disposed at the distal end. A plurality of conductive wires electrically couple at least one of the plurality of electrodes to at least one of the plurality of terminals.

16 Claims, 9 Drawing Sheets

(51) Int. Cl.
*A61N 1/04* (2006.01)
*A61N 1/36* (2006.01)

(56) References Cited

U.S. PATENT DOCUMENTS

| | | | |
|---|---|---|---|
| 5,095,916 A | 3/1992 | Smits | |
| 5,411,025 A | 5/1995 | Webster, Jr. | |
| 5,628,313 A | 5/1997 | Webster, Jr. | |
| 5,782,239 A | 7/1998 | Webster, Jr. | |
| 6,575,968 B1 | 6/2003 | Eggers et al. | |
| 6,687,549 B1 | 2/2004 | Helland et al. | |
| 7,174,219 B2 | 2/2007 | Wahlstrand et al. | |
| 7,177,702 B2* | 2/2007 | Wallace et al. | |
| 8,224,456 B2* | 7/2012 | Daglow ............... A61N 1/0551 607/116 | |
| 2003/0212446 A1 | 11/2003 | Kaplan et al. | |
| 2004/0059392 A1 | 3/2004 | Parramon et al. | |
| 2004/0098074 A1 | 5/2004 | Erickson et al. | |
| 2004/0122499 A1 | 6/2004 | Westlund | |
| 2005/0070983 A1 | 3/2005 | Rugnetta et al. | |
| 2005/0203600 A1 | 9/2005 | Wallace et al. | |
| 2005/0203602 A1 | 9/2005 | Wallace et al. | |
| 2005/0222647 A1 | 10/2005 | Wahlstrand et al. | |
| 2006/0095088 A1 | 5/2006 | De Ridder | |
| 2006/0100671 A1 | 5/2006 | Ridder | |
| 2006/0116742 A1 | 6/2006 | De Ridder | |
| 2006/0149335 A1 | 7/2006 | Meadows | |
| 2006/0149336 A1 | 7/2006 | Meadows | |
| 2006/0168805 A1 | 8/2006 | Hegland et al. | |
| 2006/0173262 A1 | 8/2006 | Hegland et al. | |
| 2006/0259110 A1 | 11/2006 | Wallace et al. | |
| 2007/0150034 A1 | 6/2007 | Rooney et al. | |
| 2007/0203540 A1 | 8/2007 | Goetz et al. | |
| 2007/0203542 A1 | 8/2007 | Goetz et al. | |
| 2007/0203543 A1 | 8/2007 | Stone et al. | |
| 2007/0203546 A1 | 8/2007 | Stone et al. | |
| 2007/0213795 A1 | 9/2007 | Bradley et al. | |
| 2008/0147158 A1 | 6/2008 | Zweber et al. | |
| 2008/0243218 A1 | 10/2008 | Bottomley et al. | |

FOREIGN PATENT DOCUMENTS

| | | |
|---|---|---|
| WO | 2004002288 | 1/2004 |
| WO | 2005092432 | 10/2005 |
| WO | 2005102446 | 11/2005 |
| WO | 2006047265 | 5/2006 |
| WO | 2006083881 | 8/2006 |
| WO | 2006083884 | 8/2006 |
| WO | 2006133445 | 12/2006 |
| WO | 2007100427 | 8/2007 |
| WO | 2007097860 | 8/2007 |
| WO | 2007097873 | 8/2007 |
| WO | 2007100428 | 9/2007 |
| WO | 2008115426 | 9/2008 |

OTHER PUBLICATIONS

Official Communication for U.S. Appl. No. 12/237,888 dated Mar. 5, 2013.
Official Communication for U.S. Appl. No. 12/237,888 dated May 8, 2014.
Official Communication for U.S. Appl. No. 12/237.888 dated Nov. 19, 2014.

* cited by examiner

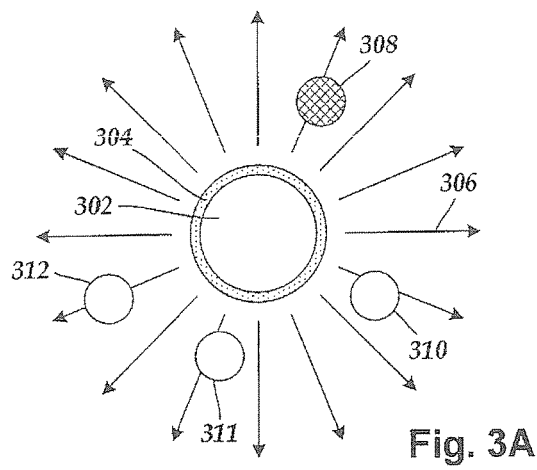
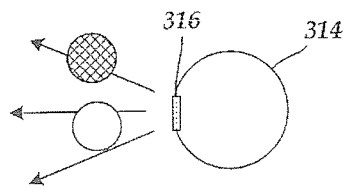
Fig. 3A
Fig. 3B
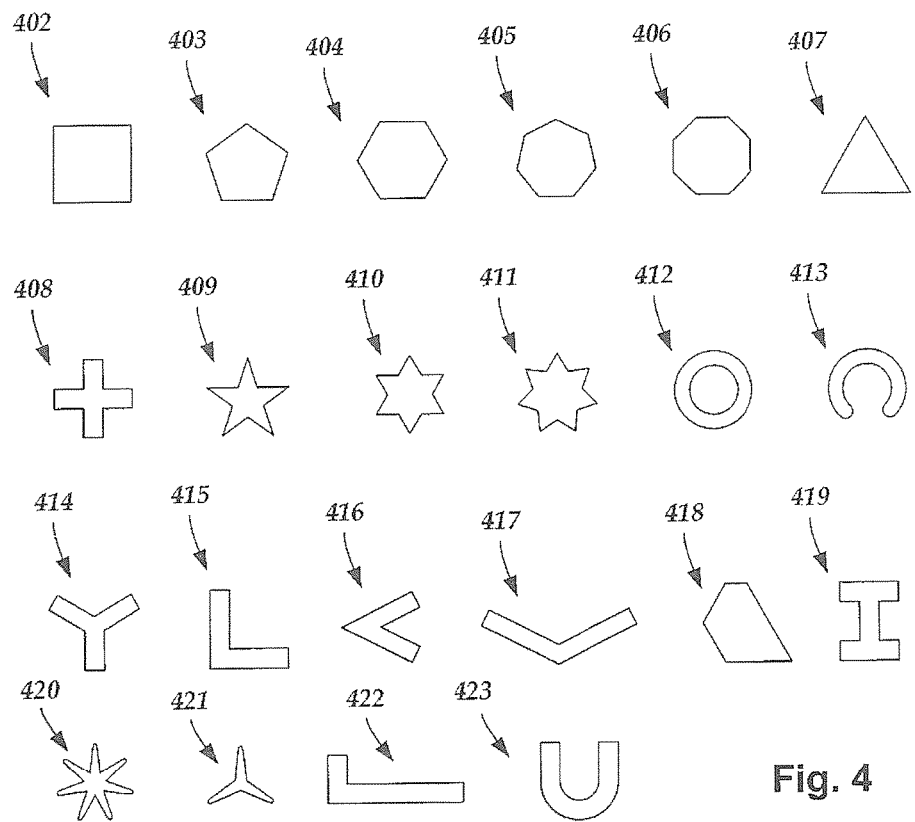
Fig. 4

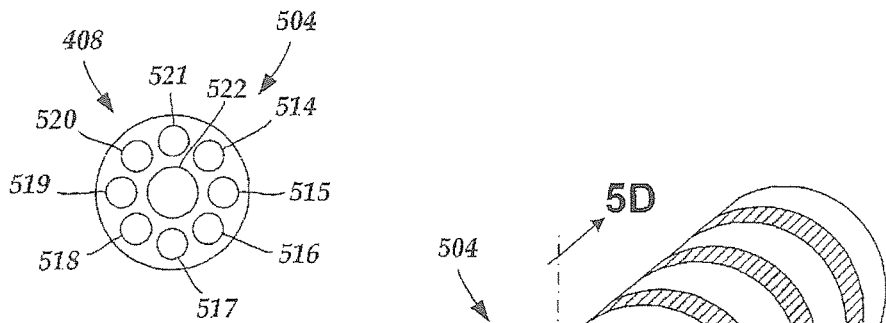
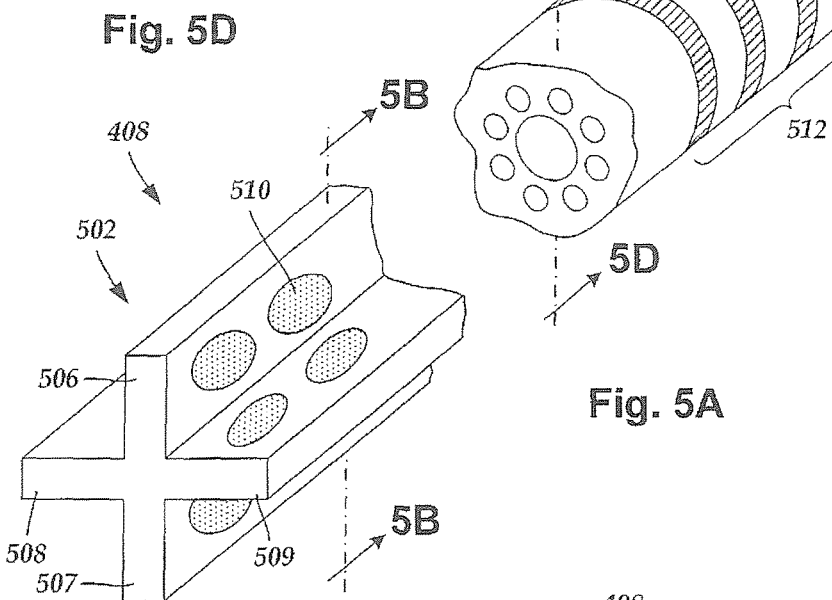
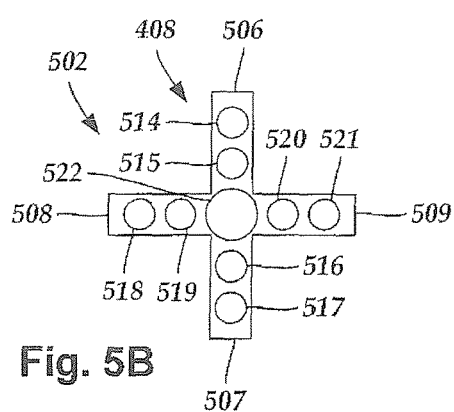
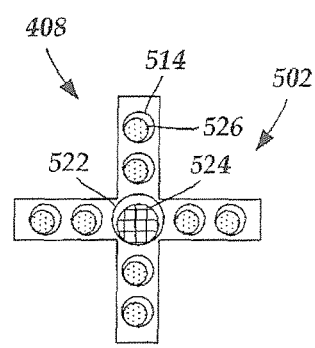

LEADS WITH NON-CIRCULAR-SHAPED DISTAL ENDS FOR BRAIN STIMULATION SYSTEMS AND METHODS OF MAKING AND USING

CROSS-REFERENCE TO RELATED APPLICATIONS

This patent application is a continuation of U.S. patent application Ser. No. 12/237,888 filed on Sep. 25, 2008, which is incorporated herein by reference.

TECHNICAL FIELD

The present invention is directed to the area of brain stimulation systems and methods of making and using the systems. The present invention is also directed to brain stimulation systems that include leads with distal ends that have non-circular transverse cross-sectional shapes configured and arranged to limit stimulation to one or more discrete stimulation regions, as well as methods of making and using the leads and brain stimulation systems.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to target structures, such as neurons. To further refine the position, a recording lead with a recording electrode at or near the tip of the recording lead can be inserted into the brain of the patient to determine a more precise location. Typically, the recording lead is guided to the target location within the brain using a stereotactic frame and microdrive motor system.

As the recording lead is moved through the brain, the recording electrode is observed to determine when the recording electrode is near the target structures. This observation may include activating the target structures to generate electrical signals that can be received by the recording electrode. Once the position of the target structures is determined, the recording lead can be removed and the stimulating lead inserted. The object of this removal of the recording lead and insertion of the stimulating lead is to attempt to precisely locate the target structures. The precise insertion of the stimulating lead and positioning of the stimulating lead in the precise location indicated by the recording lead can be particularly difficult. In some instances, multiple insertions of the recording lead and stimulating lead may need to occur to properly position the stimulating electrode.

BRIEF SUMMARY

In one embodiment, a lead is configured and arranged for brain stimulation. The lead includes a proximal end and a distal end. The proximal end includes a plurality of terminals disposed at the proximal end. The distal end has a non-circular transverse cross-sectional shape and includes a plurality of electrodes disposed at the distal end. A plurality of conductive wires electrically couple at least one of the plurality of electrodes to at least one of the plurality of terminals.

In another embodiment, a lead is configured and arranged for brain stimulation. The lead includes a proximal end and a distal end. The proximal end includes a plurality of terminals disposed at the proximal end. The distal end includes a plurality of electrodes disposed at the distal end. The distal end also defines a hollow interior region that is open at the distal end. The hollow interior region has a longitudinal length, an outer surface external to the hollow interior region, and an inner surface lining the sides of the hollow interior region. A plurality of conductive wires electrically couple at least one of the plurality of electrodes to at least one of the plurality of terminals.

In yet another embodiment, a method for stimulating patient brain tissue includes implanting a lead into a brain of a patient. The lead includes a plurality of electrodes disposed on a distal end. The distal end has a non-circular transverse cross-sectional shape. The plurality of electrodes are electrically coupled to a plurality of terminals disposed on a proximal end. A plurality of conductive wires electrically couple at least one terminal to at least one electrode. The proximal end of the lead is disposed into a connector. The connector is configured and arranged for receiving the proximal end of the lead. The connector includes a plurality of connective contacts that electrically couple to at least one of the plurality of terminals. The connector is electrically coupled to a control module. Electrical signals are provided from the control module to electrically stimulate patient tissue using at least one of the plurality of electrodes disposed on the distal end of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a schematic cross-sectional view of one embodiment of a distal end of a conventional lead with a circular transverse cross-sectional shape, the lead having a ring-shaped electrode emitting signals, shown as arrows projecting outward from the electrode, some of which are stimulating a target structure, shown with a crisscross hatching, as well as several non-target structures, according to the invention;

FIG. 3B is a schematic cross-sectional view of one embodiment of a distal end of a conventional lead with a circular transverse cross-sectional shape, the lead having a discretely-shaped electrode disposed on one side of the lead that is emitting signals, shown as arrows projecting outward from the electrode, and stimulating a target structure, shown with a crisscross hatching, as well as a non-target structure, according to the invention;

FIG. 4 is a schematic end view of a plurality of different embodiments of distal ends of leads, each distal end having a different transverse cross-sectional shape from the other distal ends, according to the invention;

FIG. 5A is a schematic perspective view of one embodiment of a lead with electrodes disposed on a plus-shaped distal end and terminals disposed on a circular-shaped proximal end; according to the invention;

FIG. 5B is a schematic transverse cross-sectional view of one embodiment of a distal end of the lead shown in FIG. 5A with two attached arms, the lead including a central lumen defined at the intersection of the two arms and peripheral lumens defined along each arm distal to the central lumen, according to the invention;

FIG. 5C is a schematic transverse cross-sectional view of one embodiment of a distal end of the lead shown in FIG. 5A with an insertion rod of a stylet disposed in a central lumen and a connector wire disposed in each of the peripheral lumens, according to the invention;

FIG. 5D is a schematic transverse cross-sectional view of a proximal end of the lead shown in FIG. 5A, the lead defining a central lumen and also defining peripheral lumens disposed lateral to the central lumen, according to the invention;

DETAILED DESCRIPTION

The present invention is directed to the area of brain stimulation systems and methods of making and using the systems. The present invention is also directed to brain stimulation systems that include leads with distal ends that have non-circular transverse cross-sectional shapes configured and arranged to limit stimulation to one or more stimulation regions, as well as methods of making and using the leads and brain stimulation systems.

A lead for deep brain stimulation can include both recording and stimulation electrodes. This allows a practitioner to determine the position of the target structures, such as neurons, using the recording electrode(s) and then position the stimulation electrode(s) accordingly without removal of a recording lead and insertion of a stimulation lead. A lead can also include recording electrodes spaced around the circumference of the lead to more precisely determine the position of the target structures. In at least some embodiments, the lead is rotatable so that the stimulation electrodes can be aligned with target structures after the neurons have been located using the recording electrodes.

Figure 1:
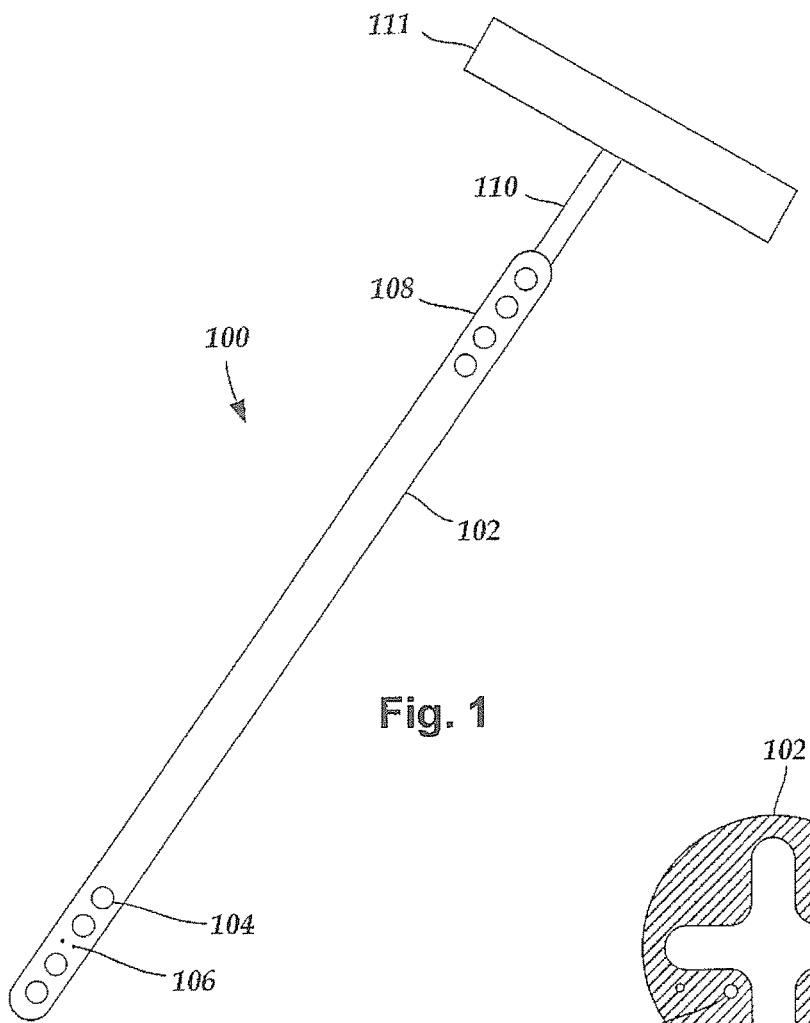
FIG. 1 is a schematic side view of one embodiment of a lead and stylet, according to the invention.

FIG. 1 illustrates one embodiment of a device 100 for brain stimulation. The device includes a lead 102, one or more stimulation electrodes 104, one or more recording electrodes 106, a connector 108 for connection of the electrodes to a control module, and a stylet 110 for assisting in insertion and positioning of the lead in the patient's brain.

The lead 102 can be formed of a non-conducting material such as, for example, a polymeric material. Suitable polymeric materials include, for example, silicone rubber and polyethylene. Preferably, the lead is made using a biocompatible material. In at least some instances, the lead may be in contact with body tissue for extended periods of time.

The lead often has a cross-sectional diameter of no more than 1.5 mm and may be in the range of 0.7 to 1.3 mm. The lead often has a length of at least 10 cm and the length of the lead may be in the range of 30 to 70 cm.

The lead typically defines a lumen 120 (see FIG. 2A) within the lead for the removable stylet 110. Use of a stylet can facilitate insertion of the lead into the cranium and brain tissue and facilitate positioning the lead to stimulate the target neurons. The stylet can provide rigidity to the lead during the insertion process.

Figure 2A:
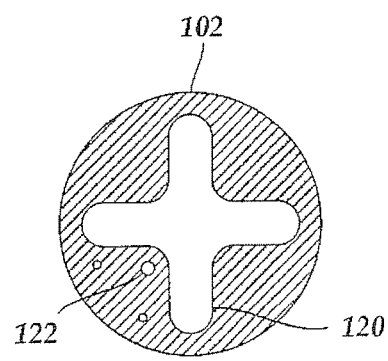
FIG. 2A is a schematic cross-sectional view of one embodiment of a lead with a plus-shaped lumen, according to the invention.
Figure 2B:
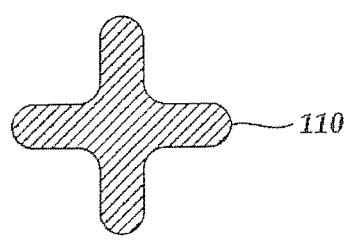
FIG. 2B is a schematic cross-sectional view of one embodiment of a stylet for use with the lead shown in FIG. 2A, according to the invention.

The lumen can have any shape. In at least some embodiments, the lumen has a round transverse cross-sectional shape. In at least some other embodiments, the transverse cross-sectional shape of the lumen is non-circular. For example, the transverse cross-sectional shape of the lumen can have an oval, square, rectangular, or, as illustrated in FIG. 2A, a cruciform shape. The stylet 110 may have a corresponding transverse cross-sectional shape. In at least some embodiments, a stylet 110 has a round transverse cross-sectional shape for use with a lead with a corresponding round transverse cross-sectional shape. In at least some embodiments, the stylet 110 may have an oval, square, rectangular, or, as illustrated in FIG. 2B, a cruciform transverse cross-sectional shape for use with the lead illustrated in FIG. 2A. Employing a non-circular transverse cross-sectional shape can permit the practitioner to rotate the lead 102 by rotating the stylet 110. Because the lumen is non-circular, the stylet can not rotate within the lead and, therefore, rotation of the stylet results in rotation of the lead. A cruciform-shaped lumen can be particularly useful, as opposed to an oval, square, or rectangular lumen, if the shape of the lumen might be deformed by rotation of the stylet because the lead is not sufficiently rigid. Shapes similar to a cruciform, with multiple arms extending from a central cavity, such as an asterisk- or star-shaped lumen and a corresponding stylet, can be similarly useful.

The stylet 110 can be made of a rigid material. Examples of suitable materials include tungsten, stainless steel, or plastic. The stylet 110 may have a handle 111 to assist insertion into the lead, as well as rotation of the stylet and lead.

Conductors 122 (e.g., wires) that attach to or form the recording electrode(s) 106 and stimulation electrode(s) 104 also pass through the lead 102. These conductors may pass through the material of the lead as illustrated, for example, in one configuration for FIG. 2A, or through the lumen 120 or through a second lumen defined by the lead. The conductors 122 are presented at the connector 108 for coupling of the electrodes 104, 106 to a control module (not shown). The control module observes and records signals from the recording electrodes 106. The same or a different control module can also be used to provide stimulation signals, often in the form of pulses, to the stimulation electrodes 104.

The lead 102 includes one or more recording electrodes 106 disposed along the longitudinal axis of the lead near a distal end of the lead. In at least some embodiments, the lead includes a plurality of recording electrodes. The recording electrodes can be made using a metal, alloy, conductive oxide, or other conductive material. Examples of suitable materials include platinum, iridium, platinum iridium alloy, stainless steel, titanium, and tungsten.

Any type of recording electrode can be used, including monopolar recording electrodes, bipolar recording electrodes (as illustrated in FIG. 1), and other multipolar recording electrodes. In at least some embodiments, bipolar or other multipolar recording electrodes are preferred because they can assist in finding nearby electrical signals, and disregard distant electrical signals, by observation of the differential between the signals from the two or more, closely-spaced electrodes.

Any type of recording electrode can be used including electrode pads or plates. A preferred recording electrode for at least some embodiments is a tip of a wire. This type of electrode can assist in more precise location of the target neurons because of the small surface area and high impedance for detection of electrical signals. Such recording electrodes often have a diameter of no more than 100 µm and no less than 25 µm. The diameter may be in the range from, for example, 25 µm to 100 µm. In one embodiment, the recording electrodes 106 correspond to wire conductors 122 that extend out of the lead 102 and are then trimmed or ground down flush with the lead surface.

The lead 102 also includes one or more stimulation electrodes 104 arranged along the longitudinal axis of the lead near a distal end of the lead. In at least some embodiments, the lead includes a plurality of stimulation electrodes. A conductor 122 is attached to each stimulation electrode 104. The stimulation electrodes often have a surface area of at least 1 mm$^2$ and no greater than 6 mm$^2$. The surface area may be in the range from, for example, 1 mm$^2$ to 6 mm$^2$. A variety of shapes can be used for the stimulation electrodes including, for example, rings, circles, ovals, squares, rectangles, triangles, and the like. In some embodiments, a stimulation electrode 104 forms a ring, or other closed-loop shape, that fully or substantially encircles the lead 102. Preferably, however, the stimulation electrodes are not rings, but are instead discrete shapes disposed on one side of the lead. Ring electrodes typically stimulate target structures on all sides of the lead instead of focusing on the target structures that may face only a portion of the lead circumference.

The stimulation electrodes can be made using a metal, alloy, conductive oxide or other conductive material. Examples of suitable materials include platinum, iridium, iridium oxide, platinum iridium alloy, stainless steel, titanium, tungsten, or poly(3,4-ethylenedioxythiophene (PEDOT). Preferably, the stimulation electrodes are made of a material that is biocompatible and does not substantially corrode under expected operating conditions in the operating environment for the expected duration of use.

The arrangement of recording electrodes 106 and stimulation electrodes 104 on the lead 102 can facilitate detection and stimulation of target structures, such as neurons. Some embodiments include a single recording electrode and a single stimulation electrode. Other embodiments, however, include two or more recording electrodes, two or more stimulation electrodes, or both.

Sometimes conventional brain stimulation systems employ leads with a circular transverse cross-sectional shape. Leads with a circular transverse cross-sectional shape may include one or more rings of stimulation electrodes ("electrodes") disposed on distal ends of the leads that emit signals, such as pulses of electric current, in all directions around the distal ends of the leads. Target structures within a certain distance from the one or more rings of signal-emitting electrodes can be stimulated by the signals. However, some non-target structures may also be positioned so as to also be stimulated.

FIG. 3A shows a schematic end view of one embodiment of a conventional lead 302 for a brain stimulation system. The lead 302 has a circular transverse cross-sectional shape and includes one or more cylindrical electrodes 304 emitting signals, shown as arrows such as arrow 306, projecting outward from the one or more cylindrical electrodes 304. The signals are of approximately equal strength in all directions normal to the lead 302. In FIG. 3A, a target structure 308, shown in FIG. 3A and in subsequent figures as a circle with a crisscrossed hatching, is shown being stimulated by the lead 302. However, other non-target structures 310-312, are also being stimulated by the lead 302. In at least some instances, stimulating non-target structures may be undesirable and may cause one or more negative effects on a patient, such as producing patient pain, vision problems, speech problems, or cognitive problems. As discussed above, with reference to FIG. 1, some conventional leads utilize electrodes with discrete shapes disposed along one side of the lead, such as the lead 314 shown in FIG. 3B. However, electrodes disposed along one side of a lead with a circular transverse cross-sectional shape, such as the electrode 316 disposed on the lead 314, may not offer much variance in the directionality of signal emission.

In at least some embodiments, a lead compatible with a brain stimulation system includes electrodes selectively disposed on a non-circular transverse cross-sectional shaped distal end of the lead so that the electrodes can emit signals within one or more stimulation regions of different sizes and shapes. For example, target structures can be stimulated in stimulation regions and non-target structures in other regions can avoid being stimulated. In at least some embodiments, the transverse cross-sectional shape of the distal end of the lead may affect one or more variables of signals emitted from the electrodes, such as the direction of the signal emission, or the amplitude, or strength, of the signal emission.

In at least some embodiments, de-activation of one or more electrodes disposed on the lead may also affect one or more variables of signals emitted from the electrodes, such as the direction of the signal emission, or the strength of the signal emission. In at least some embodiments, providing electrodes of various sizes and shapes may further affect one or more variables of signals emitted from the electrodes, such as the direction of the signal emission, or the strength of the signal emission. In at least some embodiments, when multiple regions are stimulated, each stimulation region may utilize different stimulation parameters from other stimulation regions. In at least some embodiments, when there are multiple stimulation regions, each of the multiple stimulation regions may be stimulated individually, simultaneously, or sequentially.

In at least some embodiments, a distal end of a lead may include a non-circular transverse cross-sectional shape configured and arranged to limit signals emitted from one or more electrodes disposed on the distal ends of the leads to selected stimulation regions. FIG. 4 is a schematic end view of a plurality of different embodiments of the transverse cross-sectional shape of distal ends of leads 402-423 on which electrodes may be disposed. The distal ends of the leads 402-423 each include a transverse cross-sectional shape that is different from the other remaining leads 402-423. Many different transverse cross-sectional shapes may be selected that are either regular or irregular shapes, with straight edges or curved edges. A few exemplary transverse cross-section shapes of distal ends of suitable leads are shown in FIG. 4, including a rectangle 402, a pentagon 403, a hexagon 404, a heptagon 405, an octagon 406, a triangle 407, a cruciform-shape 408, a five-pointed star 409, a six-pointed star 410, a seven-pointed star 411, a cylinder-shape 412, a C-shape 413, a Y-shape 414, an L-shape 415 with arms of approximately equal length, an acutely-angled V-shape 416, an obtusely-angled V-shape 417, an irregular pentagon 418, an I-shape 419, an alternate seven-pointed star with elongated arms 420, an alternate triangle with elongated arms 421, an L-shape 422 with arms of unequal length, and a U-shape 423.

In at least some embodiments, the sizes and the distributions of the target structures may affect the selection of shape of the lead to use for stimulation. In at least some embodiments, the lead selected may have a transverse cross-sectional shape that limits the one or more stimulation regions of the lead to the smallest possible regions that collectively stimulate the one or more desired target structures. In at least some embodiments, some of the leads include transverse cross-sectional shapes that have at least two attached arms that can form different angles with each other, such as shapes 414-417, and 419-422. Moreover, in at least some embodiments, the arms may be of variable lengths, for example, shape 411 compared to shape 420, and shape 415 compared to shape 422. It will be understood that other transverse cross-sectional shapes shown in FIG. 4 with multiple arms may be altered by increasing or decreasing one or more of the angles between two of the arms. Additionally, it will be understood that other transverse cross-sectional shapes shown in FIG. 4 with multiple arms may be altered by increasing or decreasing the length one or more of the arms. Moreover, it will be understood that the shapes may be smoothed to facilitate manufacturing or safety in patient tissue.

In at least some embodiments, a lead with a non-circular transverse cross-sectional shaped distal end, such as the leads 402-423, may have a circular transverse cross-sectional shaped proximal end. In at least some embodiments, a lead with a circular transverse cross-sectional shaped proximal end may facilitate electrical connection of the lead with a control module. Additionally, in at least some embodiments, when a lead includes a non-circular transverse cross-sectional shaped distal end and a circular transverse cross-sectional shaped proximal end, both ends of the lead are configured and arranged for implantation using conventional insertion needles and guide cannulas used for electrical stimulation systems, such as brain stimulation systems.

FIG. 5A is a schematic perspective view of a lead 408. The lead 408 includes a distal end 502 that has a cruciform-shaped transverse cross-sectional shape and a proximal end 504 that has a circular transverse cross-sectional shape. The distal end 502 of the lead 408 includes arms 506-509. Each arm 506-509 includes electrodes, such as electrode 510, disposed on the distal end 502 of the lead 408. The proximal end 504 of the lead 408 includes terminals 512.

In at least some embodiments, the electrodes disposed on the lead 408 may be disposed on one or more sides of one or more of the arms 506-509. In at least some embodiments, one or more of the arms may include electrodes disposed in one or more rows or columns. In at least some embodiments, the electrodes may be disposed in rows or columns in either a regular or irregular pattern. In at least some embodiments, the electrodes may be disposed in rows or columns in a regular pattern, such as a level or staggered pattern.

FIG. 5B is a schematic transverse cross-sectional view of one embodiment of the distal end 502 of the lead 408. The arm 506 defines peripheral lumens 514 and 515. The arm 507 defines peripheral lumens 516 and 517. The arm 508 defines peripheral lumens 518 and 519. The arm 509 defines peripheral lumens 520 and 521. The lead 408 also defines a central lumen 522 at the intersection of the arms 506-509. In at least some embodiments, there is one peripheral lumen defined in each arm 506-509. In at least some embodiments, there are more than two lumens defined in each arm 506-509. In at least some embodiments, the central lumen 522 and the peripheral lumens 514-521 are replaced by a single lumen.

FIG. 5C is a schematic transverse cross-sectional view of one embodiment of the distal end 502 of the lead 408 with an insertion rod 524 of a stylet disposed in the central lumen 522 and a connector wire disposed in each peripheral lumen, such as connector wire 526 disposed in the peripheral lumen 514. FIG. 5D is a schematic transverse cross-sectional view of one embodiment of the proximal end 504 of the lead 408. The proximal end 504 of the lead 408 defines the central lumen 522 and the peripheral lumens 514-521 disposed laterally from the central lumen 522.

In at least some embodiments, the shape of the distal end of the lead 408, as well as the positioning of the one or more electrodes on the distal end of the lead 408 and the selected de-activation of one or more particular electrodes, may affect one or more variables of signals emitted from the electrodes, such as the direction of the signal emission, or the strength of the signal emission.

Figure 6A:
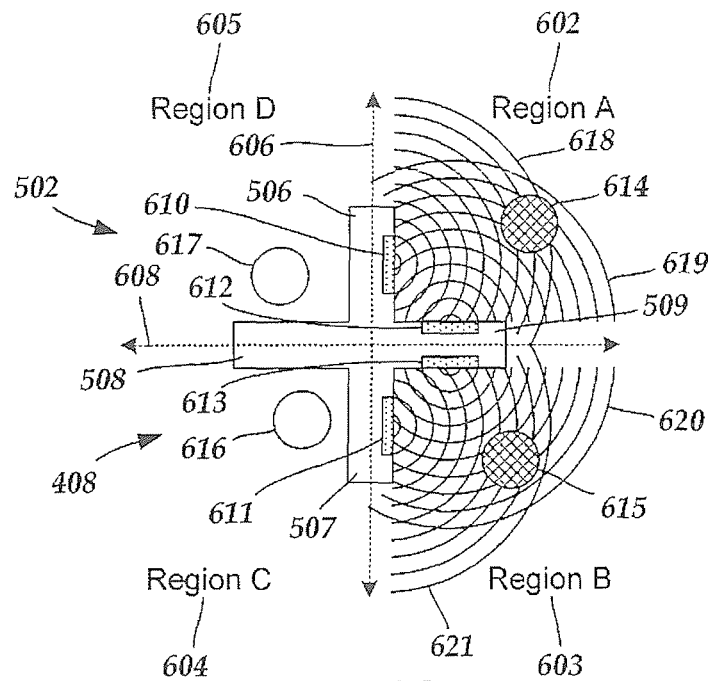
FIG. 6A is a schematic transverse cross-sectional view of one embodiment of a distal end of the lead shown in FIG. 5A positioned in an area divided into regions, the lead having electrodes emitting signals that are stimulating target structures positioned in two stimulation regions and not stimulating non-target structures positioned in other regions, according to the invention.

Changing the variables of the signals emitted from the electrodes, such as the direction of the signal emission or the strength of the signal emission may, in turn, affect the size and shape of a stimulation region. FIG. 6A is a schematic transverse cross-sectional view of one embodiment of the distal end 502 of the lead 408. The lead 408 includes the arms 506-509. The lead 408 is positioned in an area divided into regions 602-605 based, at least in part, on the shape of the distal end 502 of the lead 408. For example, in FIG. 6A, "Region A" 602, "Region B" 603, "Region C" 604, and "Region D" 605 are defined along perpendicular axes 606 and 608 extending along the arms 506 and 508 of the distal end 502 of the lead 408.

The electrodes can be positioned anywhere along any of the arms 506-509. For example, in FIG. 6A the arm 506 includes the electrode 610, the arm 507 includes the electrode 611, the arm 508 includes two electrodes 612 and 613, and the arm 508 does not include any electrodes. In FIG. 6A, the electrodes 610-613 are positioned so that two of the electrodes 610 and 612 are facing "Region A" 602 and two of the electrodes 611 and 613 are facing "Region B" 603, while no electrodes are facing either "Region C" 604 or "Region D" 605.

In FIG. 6A, the regions 602 and 603 each contain a target structure 614 and 615, respectively, and the regions 604 and 605 each contain a non-target structure 616 and 617, respectively. In at least some embodiments, the distal end 502 of the lead 408 can be positioned so that target structures 614 and 615 are located in proximity to the portions of the lead 408 containing electrodes. Accordingly, in FIG. 6A, the target structures are located in "Region A" 602 and "Region B" 603, but not in "Region C" 604 or "Region D" 605. The "Region A" 602 and "Region 13" 603 are stimulation regions and "Region C" 604 and "Region D" 605 are not.

In at least some embodiments, the electrodes 610-613 may emit signals 618-621 in the stimulation regions, thereby stimulating the target structures 614 and 615, without stimulating the non-target structures 616 and 617. In alternate embodiments, a similar emission pattern may be achieved by de-activation of selected electrodes. For example, in at least some embodiments, each of the arms 506-509 may include one or more electrodes and the electrodes facing "Region C" 604 and "Region D" 605 may be de-activated.

Figure 6B:
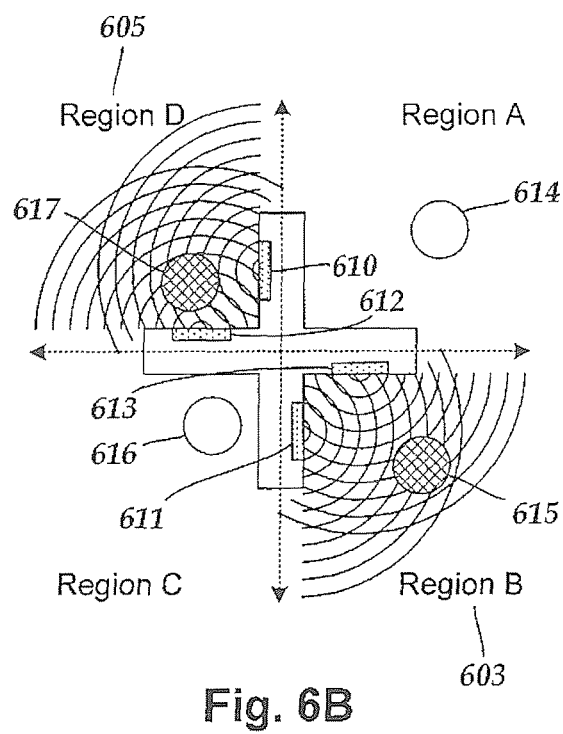
FIG. 6B is a schematic transverse cross-sectional view of another embodiment of a distal end of the lead shown in FIG. 5A positioned in an area divided into regions, the lead having electrodes emitting signals that are stimulating target structures positioned in two stimulation regions and not stimulating non-target structures positioned in other regions, according to the invention.

In alternate embodiments, the electrodes 610-613 may be disposed at other locations along the arms 506-509 in order to stimulate target structures in other regions. For example, in FIG. 6B, the target structures 615 and 617 are located in "Region B" 603 and "Region D" 605. Thus, the electrodes 610-613 can be positioned so that "Region B" 603 and "Region D" 605 are the stimulation regions, while the other regions are not. Hence, target structures 615 and 617 can be stimulated without stimulating the non-target structures 614 and 616. In other alternate embodiments, two or more electrodes may be positioned to provide stimulation in any one or more of the regions 602-605, while not providing stimulation in the remaining regions 602-605. In at least some embodiments, when more than one region 602-605 is being stimulated, different stimulation parameters can be applied to each stimulation region. For example, in FIG. 6B a first current can be applied to the target structure 615 in "Region B" 603, while a second current that is different from the first current can be applied to the target structure 617 in "Region D" 605. It will be understood that a similar emission pattern may be achieved by disposing electrodes in each of the regions and selectively de-activating one or more of the electrodes in one or more non-selected regions.

Figure 7A:
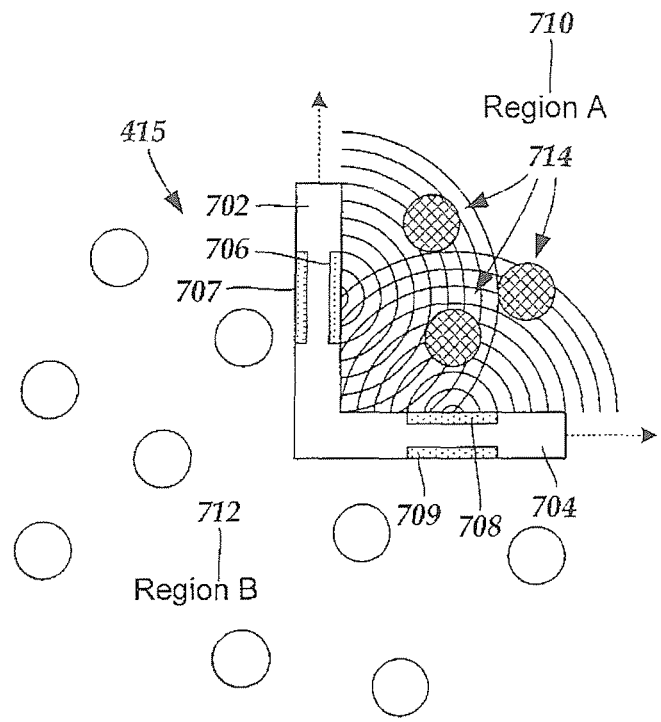
FIG. 7A is a schematic transverse cross-sectional view of one embodiment of a distal end of one of leads shown in FIG. 4 positioned in an area divided into regions, the lead having electrodes emitting signals that are stimulating target structures positioned in one stimulation region and not stimulating non-target structures positioned in the other region, according to the invention.
Figure 7B:
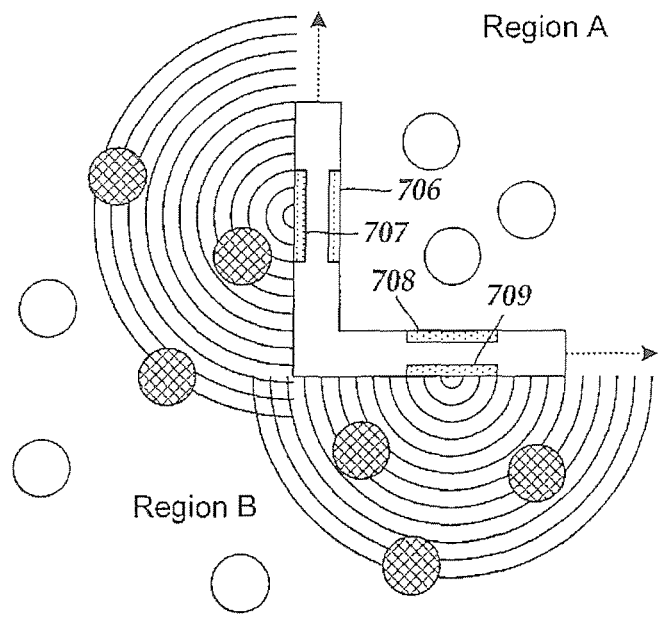
FIG. 7B is a schematic transverse cross-sectional view of another embodiment of a distal end of one of leads shown in FIG. 4 positioned in an area divided into regions, the lead having electrodes emitting signals that are stimulating target structures positioned in one stimulation region and not stimulating non-target structures positioned in the other region, according to the invention.

FIG. 7A is a schematic transverse cross-sectional view of one embodiment of a distal end of the lead 415. The lead 415 has an L-shaped distal end that includes arms 702 and 704. The lead 415 also includes electrodes 706 and 707 disposed on opposite sides of the arm 702, and electrodes 708 and 709 disposed on opposite sides of the arm 704. The lead 415 is positioned in an area divided into regions "Region A" 710 and "Region B" 712 based, at least in part, on the shape of the distal end of the lead 415, the positioning of the one or more electrodes 706-709, and the activation of one or more of the electrodes 706-709. The "Region A" 710 includes target structures 714, while the "Region B" 712 does not include any target structure 714. Thus, "Region A" 710 is the stimulation region. The electrodes 706 and 708 are positioned to face "Region A" 710 and the electrodes 707 and 709 are positioned to face "Region B" 712. As shown in FIG. 7A, the electrodes 706 and 708 are emitting signals and the electrodes 707 and 709 are de-activated. As a result, target structures 714 in "Region A" 710 are being stimulated, while non-target structures in "Region B" 712 are not being stimulated. In an alternate embodiment, the electrodes 707 and 709 emit signals while the electrodes 706 and 708 are de-activated, as shown in FIG. 7B. Thus, in the alternate embodiment "Region B" 712 is the stimulation region and, accordingly, target structures in "Region B" 712 are being stimulated and non-target structures in "Region B" 708 are not being stimulated.

In at least some embodiments, providing electrodes of various sizes and shapes may affect one or more variables of signals emitted from the electrodes, such as the direction of the signal emission, or the strength of the signal emission. Changing the variables of the signals emitted from the electrodes, such as the direction of the signal emission or the strength of the signal emission may, in turn, affect the size and shape of a stimulation region. In at least some embodiments one or more electrodes are disposed on a single face of a distal end of a lead with a multi-faced transverse cross-sectional shape. In at least some embodiments, one or more electrodes are disposed on multiple faces of a distal end of a lead with a multi-faced transverse cross-sectional shape. In at least some embodiments, the directions of signal emissions from an electrode disposed on a single face may be different from the directions of signal emission from an electrode disposed on multiple-faces. Additionally, in at least some embodiments, a first electrode with a surface area that is greater than the surface area of a second electrode may produce a signal that travels a shorter distance than the second electrode.

Figure 8:
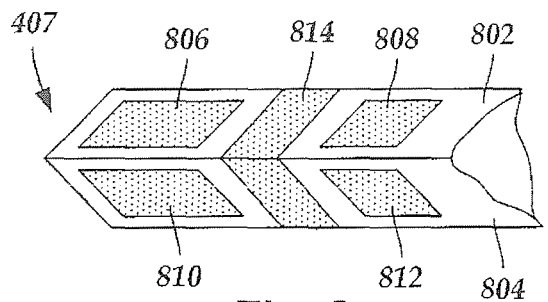
FIG. 8 is a schematic perspective view of one embodiment of a distal end of one embodiment of a distal end of one of the leads shown in FIG. 4, the lead having electrodes disposed on a triangular-shaped distal end so that some of the electrodes are disposed on multiple faces of the lead and some of the electrodes disposed on a single face of the lead, according to the invention.

FIG. 8 is a schematic perspective view of one embodiment of the lead 407 with a triangular transverse cross-sectional shape. The lead 407 includes a distal end with a triangular transverse cross-sectional shape that includes faces 802 and 804. The face 802 includes two differently-sized electrodes 806 and 808 disposed solely on the face 802. The face 804 also includes two differently-sized electrodes 810 and 812 disposed solely on the face 804 and that are approximately the same shapes, sizes, and relative locations as the electrodes 806 and 808 on the face 802. Additionally, an electrode 814 is disposed on both the faces 802 and 804. In at least some embodiments, the electrode 814 extends completely around a lateral circumference of the lead 407. In other embodiments, the electrode 814 is only disposed on two faces of the lead 407.

Figure 9:
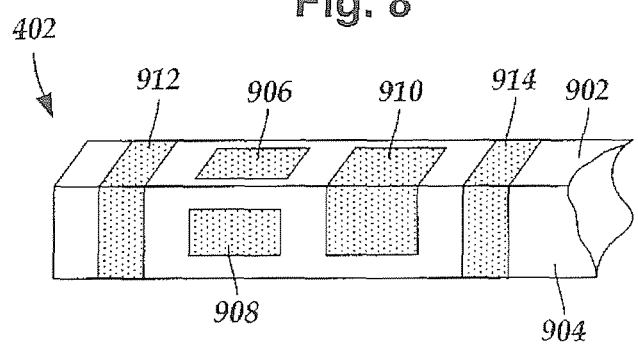
FIG. 9 is a schematic perspective view of one embodiment of a distal end of one embodiment of a distal end of one of the leads shown in FIG. 4, the lead having electrodes disposed on a rectangular-shaped distal end so that some of the electrodes are disposed on multiple faces of the lead and some of the electrodes disposed on a single face of the lead, according to the invention.

FIG. 9 is a schematic perspective view of one embodiment of the lead 402 with a rectangular transverse cross-sectional shape. The lead 402 includes a distal end with a rectangular transverse cross-sectional shape that includes faces 902 and 904. The face 902 includes an electrode 906 disposed on the face 902. Likewise, the face 904 includes an electrode 908 disposed on the face 904 that is approximately the same size, shape, and relative positioning as the electrode 906 disposed on the face 902. Additionally, an electrode 906 is disposed on both the face 902 and the face 904. Also, electrodes 912 and 914 extend completely around a lateral circumference of the lead 402. In other embodiments, the electrodes 912 and 914 are only disposed on two or three faces of the lead 402.

Figure 10A:
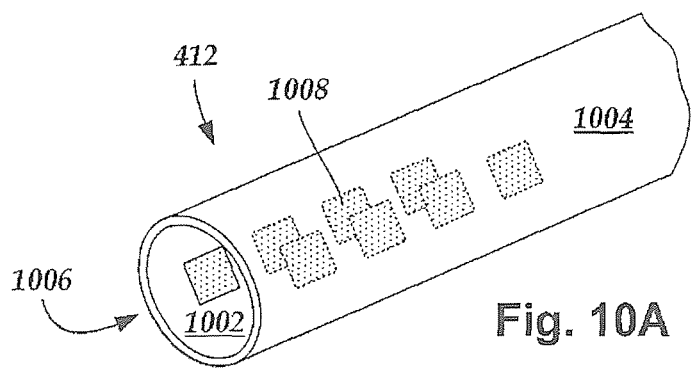
FIG. 10A is a schematic perspective view of one embodiment of one of leads shown in FIG. 4 having a with a circular transverse cross-sectional shaped distal end with electrodes disposed in linear patterns on an inner surface, according to the invention.

In at least some embodiments, target structures that are smaller in size than a diameter of a lead, such as one or more neurons, may be stimulated using a lead that includes a hollow interior region defined in a distal end of the lead. In some embodiments, the distal end may have a circular transverse cross-sectional shape. In other embodiments, the distal end may have a non-circular transverse cross-sectional shape. For example, a distal end may have a transverse cross-sectional shape that is triangular, rectangular, star-shaped, cruciform-shaped, pentagonal, hexagonal, and the like. FIG. 10A is a schematic perspective view of one embodiment of the lead 412 that includes a distal end with a circular transverse cross-sectional shape. The distal end of the lead 412 includes an inner surface 1002 and an outer surface 1004. Additionally, the distal end of the lead 412 defines a hollow interior region 1006.

In at least some embodiments, the inner surface 1002 of the distal end of the lead 412 includes at least one electrode, such as electrode 1008. Thus, the lead 412 can be positioned so that one or more target structures are disposed within the hollow interior region 1006 of the distal end of the lead 412. In at least some embodiments, when one or more target structures are disposed within the hollow interior region 1006 of the distal end of the lead 412, the hollow interior region 1006 is the stimulation region and one or more target structures may be stimulated by the electrodes disposed on the interior surface 1002 without stimulating non-target structures located in a region exterior to the lead 412.

In at least some embodiments, one or more electrodes are disposed on the outer surface 1004 of the lead 412. Thus, the lead 412 can be positioned so that one or more non-target structures are disposed within the hollow interior region 1006 of the distal end of the lead 412. In at least some embodiments, when one or more non-target structures are disposed within the hollow interior region 1006 of the distal end of the lead 412, the interior surface 1002 may either include no electrodes or include one or more electrodes that are de-activated so that the one or more non-target structures may be protected from stimulation while one or more target structures located in the region exterior to the lead 412 (the stimulation region) are stimulated.

In FIG. 10A, eight electrodes are shown arranged linearly in two matching patterns of four electrodes each disposed on opposite sides of the inner surface 1002. The number of electrodes disposed on the inner surface 1002 of the lead 412 may vary. For example, there can be two, four, six, eight, ten, twelve, fourteen, sixteen, or more electrodes. As will be recognized, other numbers of electrodes may also be used. The number of electrodes disposed into patterns on the inner surface 1002 of the lead 412 may also vary. The types of patterns into which electrodes are disposed may also vary. For example, there may be one or more linear patterns, staggered patterns, zigzag patterns, or the like or combinations thereof. Additionally, in at least some embodiments, the electrodes can be arranged, at least in part, in a non-repeating pattern, or a random pattern.

Figure 10B:
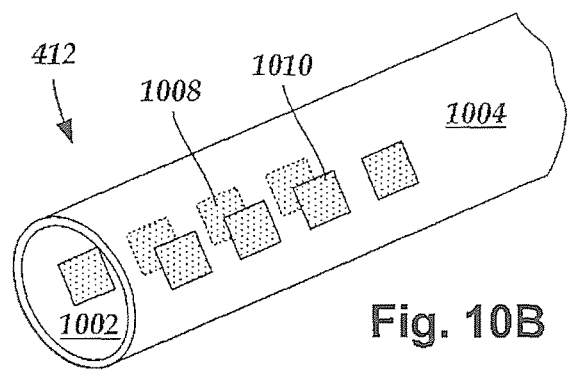
FIG. 10B is a schematic perspective view of one embodiment of the lead shown in FIG. 10A having a circular transverse cross-sectional shaped distal end with electrodes disposed in a linear pattern on both an inner surface and an outer surface, according to the invention.
Figure 10C:
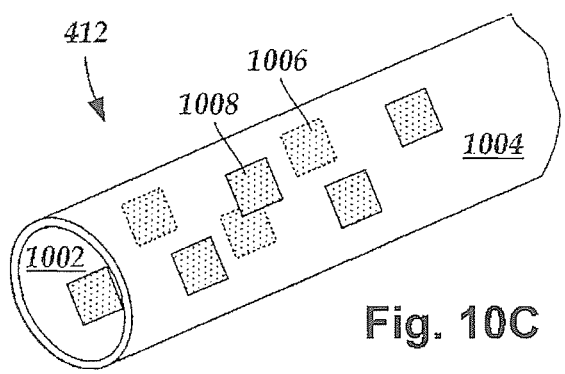
FIG. 10C is a schematic perspective view of one embodiment of the lead shown in FIG. 10A having a circular transverse cross-sectional shaped distal end with electrodes disposed in a zigzag pattern on both an inner surface and an outer surface, according to the invention.

In at least some embodiments, one or more electrodes are disposed on both the inner surface 1002 of the lead 412 and the outer surface 1004 of the lead 412. In at least some embodiments, the electrodes are disposed into patterns on the inner surface 1002 match the electrode patterns disposed on the outer surface 1004. In FIG. 10B, eight electrodes are arranged linearly in two matching patterns of four electrodes each. One of the two linearly-arranged patterns is disposed on the inner surface 1002 and includes the electrode 1008. The other of the two linearly-arranged patterns is disposed on the opposite side of the outer surface 1004 and includes the electrode 1010. FIG. 10C is a schematic perspective view of another embodiment of the lead 412. The lead 412 includes electrodes disposed on the inner surface 1002 in a zigzag pattern. The lead 412 also includes electrodes disposed on an opposite side of the lead 412 on the outer surface 1004 in a matching zigzag pattern.

Figure 10D:
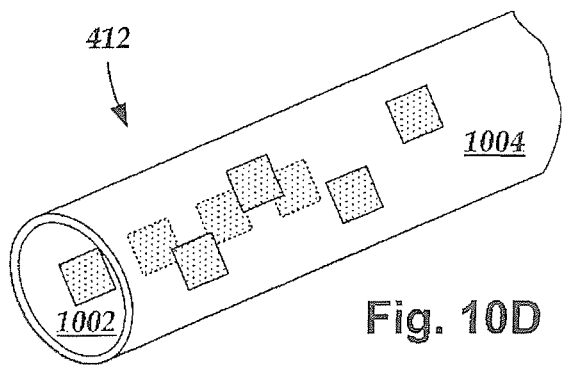
FIG. 10D is a schematic perspective view of one embodiment of the lead shown in FIG. 10A having a circular transverse cross-sectional shaped distal end with electrodes disposed in a linear pattern on an inner surface and electrodes disposed in a zigzag pattern on an outer surface, according to the invention.

In at least some embodiments, the patterns electrodes are disposed into on the inner surface 1002 do not match the patterns electrodes are disposed into on the outer surface 1004. FIG. 10D is a schematic perspective view of one embodiment or the lead 412. The lead 412 includes electrodes disposed on the inner surface 1002 in a linearly-arranged pattern and electrodes disposed on the outer surface 1004 in a zigzag pattern. In some embodiments, each of the electrodes disposed on the inner surface 1002 is disposed directly medial to an electrode disposed on the outer surface 1004. In other embodiments, at least one electrode disposed on the inner surface 1002 is not disposed directly medial to an electrode disposed on the outer surface 1004.

Figure 11A:
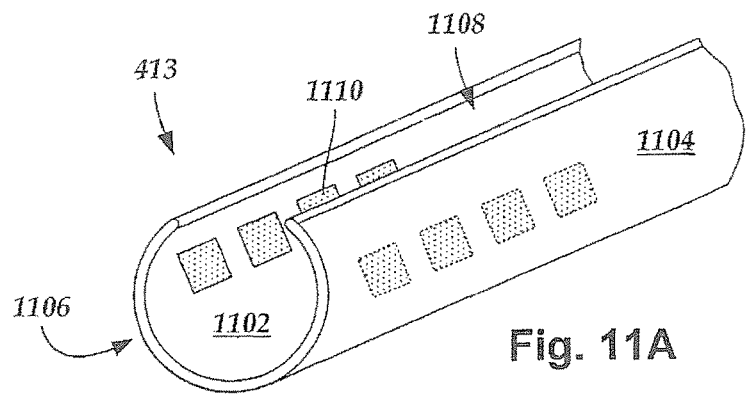
FIG. 11A is a schematic perspective view of one embodiment of one of leads shown in FIG. 4 having a C-shaped distal end with electrodes disposed in linear patterns on an inner surface, according to the invention.

Sometimes, a target structure can be more easily placed within a hollow interior region when the distal end of the lead has a C-shaped transverse cross-sectional shape instead of a circular transverse cross-sectional shape. FIG. 11A is a schematic perspective view of one embodiment of the lead 413. The lead 413 has a C-shaped transverse cross-sectional shape and includes an inner surface 1102 and an outer surface 1104. The lead 413 also includes a hollow interior region 1106 and a slit 1108 defined along at least a portion of a longitudinal length of the distal end of the lead 413. In at least some embodiments, the inner surface 1102 of the lead 413 includes at least one electrode, such as electrode 1110.

In at least some embodiments, one or more electrodes can be disposed on the lead 413 in a similar manner as the lead 412. In at least some embodiments, the lead 413 can be positioned so that one or more target structures, such as one or more neurons, are disposed within the hollow interior region 1106 of the distal end of the lead 413. In some embodiments, at least a portion of one or more target structures may extend through the slit 1108. In at least some embodiments, when one or more target structures are disposed in the hollow interior region 1106 of the distal end of the lead 413, the one or more target structures may be stimulated by the electrodes disposed on the interior surface 1102 without stimulating non-target structures located in a region exterior to the lead 413.

In at least some embodiments, one or more electrodes are disposed on the outer surface 1104 of the lead 413. Thus, the lead 413 can be positioned so that one or more non-target structures, such as one or more neurons, are disposed within the hollow interior region 1106 of the distal end of the lead 413. In at least some embodiments, when one or more non-target structures are disposed within the hollow interior region 1106 of the distal end of the lead 413, the interior surface 1102 may either include no electrodes or include one or more electrodes that are de-activated so that the one or more non-target structures may be protected from stimulation while one or more target structures located in the region exterior to the lead 413 are stimulated.

In FIG. 11A, eight electrodes are shown arranged linearly in two matching patterns of four electrodes each disposed on opposite sides of the inner surface 1102. The number of electrodes disposed on the inner surface 1102 of the lead 413 may vary. For example, there can be two, four, six, eight, ten, twelve, fourteen, sixteen, or more electrodes. As will be recognized, other numbers of electrodes may also be used. The number of electrode patterns disposed on the inner surface 1102 of the lead 413 may also vary. The types of electrode patterns may also vary. For example, there may be one or more linear patterns, staggered patterns, zigzag patterns, or the like or combinations thereof. Additionally, in at least some embodiments, the electrodes can be arranged, at least in part, in a non-repeating pattern, or a random pattern.

Figure 11B:
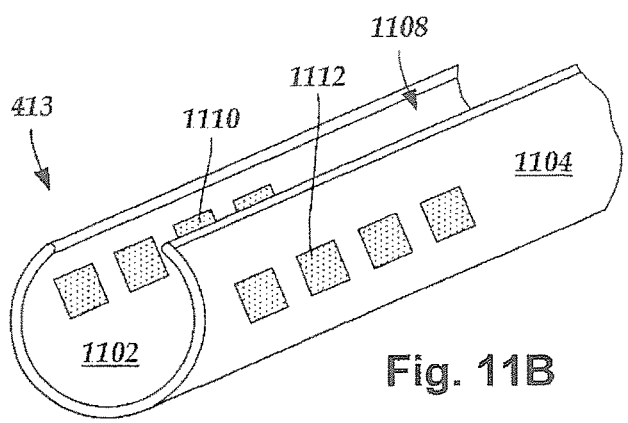
FIG. 11B is a schematic perspective view of one embodiment of the lead shown in FIG. 11A having a C-shaped distal end with electrodes disposed in a linear pattern on both an inner surface and an outer surface, according to the invention.

In at least some embodiments, one or more electrodes are disposed on both the inner surface 1102 of the lead 413 and the outer surface 1104 of the lead 413. In at least some embodiments, the electrodes are disposed into patterns on the inner surface 1102 that match the electrode patterns disposed on the outer surface 1104. In FIG. 11B, eight electrodes are arranged linearly in two matching patterns of four electrodes each. One of the two linearly-arranged patterns is disposed on the inner surface 1102 and includes the electrode 1110. The other of the two linearly-arranged patterns is disposed on the opposite side of the outer surface 1104 and includes the electrode 1012.

Figure 11C:
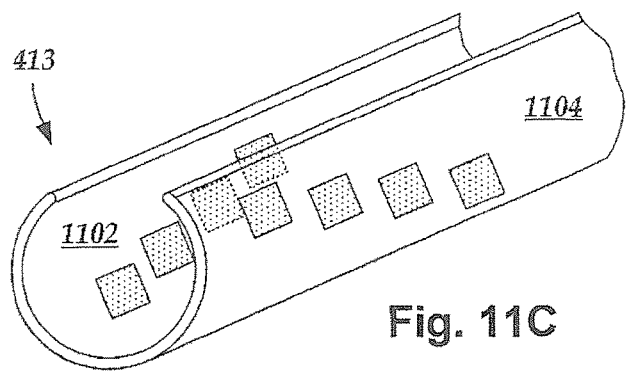
FIG. 11C is a schematic perspective view of one embodiment of the lead shown in FIG. 11A having a C-shaped distal end with electrodes disposed in a first staggered pattern on an inner surface and electrodes disposed in a second staggered patter on an outer surface, according to the invention.

In at least some embodiments, the electrode patterns disposed on the inner surface 1102 do not match the electrode patterns disposed on the outer surface 1104. FIG. 11C is a schematic perspective view of one embodiment of the lead 413. The lead 413 includes electrodes disposed into a first staggered pattern on the inner surface 1102 and electrodes disposed into a second staggered pattern on the outer surface 1104. In some embodiments, each of the electrodes disposed on the inner surface 1102 is disposed directly medial to an electrode disposed on the outer surface 1104. In other embodiments, at least one electrode disposed on the inner surface 1102 is not disposed directly medial to an electrode disposed on the outer surface 1104.

Figure 12:
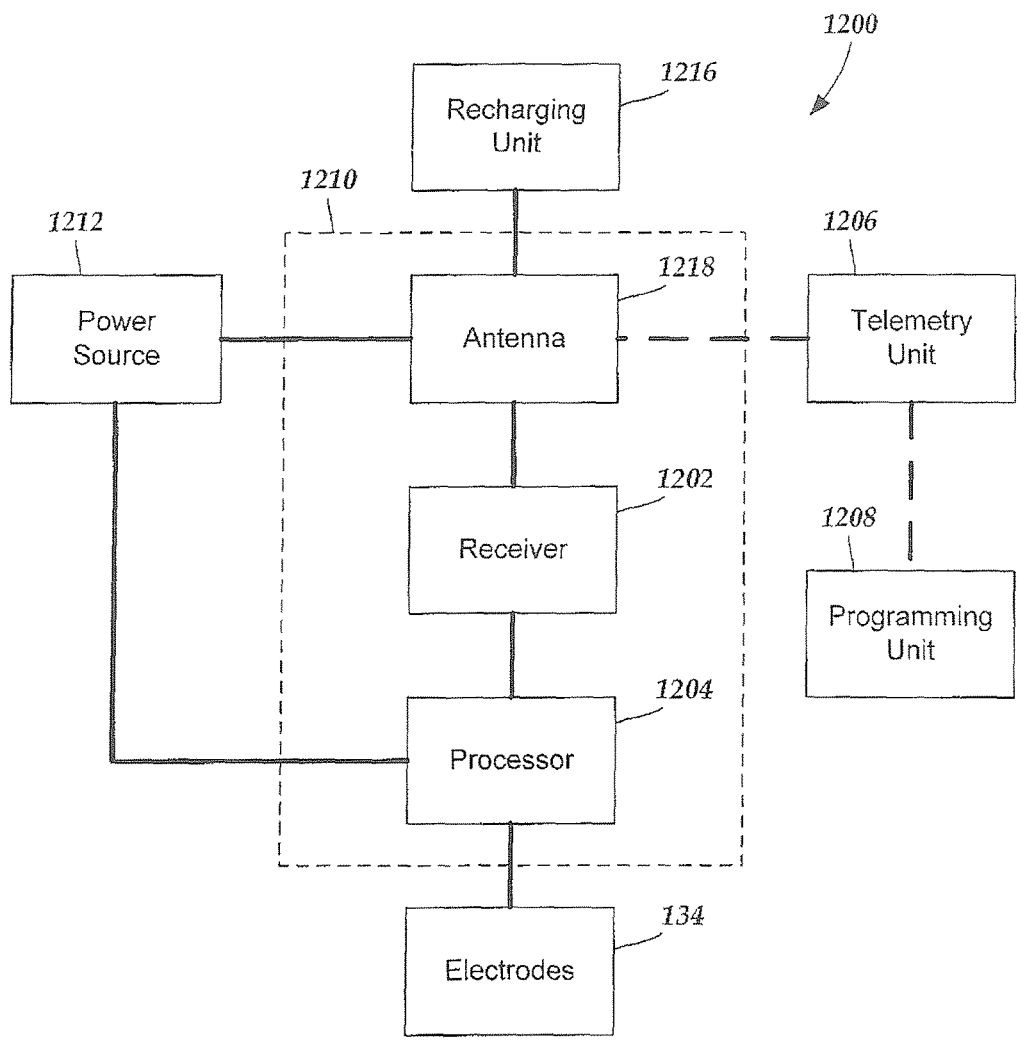
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead configured and arranged for brain stimulation, the lead comprising:
    a proximal end of the lead comprising a plurality of terminals disposed along the proximal end;
    a distal end of the lead comprising a plurality of electrodes disposed along the distal end, wherein the distal end comprises a curved wall that defines a hollow interior region within the distal end of the lead, wherein the hollow interior region is open at the distal end and has a longitudinal length, wherein the curved wall has an exterior surface and an interior surface opposite the exterior surface, the interior surface lining the hollow interior region, wherein two or more of the electrodes are disposed on the interior surface of the curved wall and exposed to the hollow interior region of the distal end of the lead; and
    a plurality of conductive wires extending along the lead and electrically coupling the plurality of electrodes to the plurality of terminals.

2. The lead of claim 1, wherein the distal end has a circular transverse cross-sectional shape.

3. The lead of claim 1, wherein the curved wall of the distal end further defines at least one slit along at least a portion of the longitudinal length of the hollow interior region, wherein the hollow interior region is open along the at least one slit.

4. The lead of claim 1, wherein all of the electrodes are disposed on the interior surface of the curved wall.

5. The lead of claim 1, wherein at least one of the electrodes is disposed on the exterior surface of the curved wall of the distal end.

6. The lead of claim 1, wherein the plurality of electrodes comprises a first set of electrodes disposed on the interior surface of the curved wall and a second set of electrodes disposed on the exterior surface of the curved wall.

7. The lead of claim 6, wherein the first and second sets of electrodes are each arranged in a linear arrangement.

8. The lead of claim 6, wherein the first set of electrodes and the second set of electrodes are arranged in different arrangements.

9. The lead of claim 6, wherein at least one of the first and second sets of electrodes is arranged in a zigzag arrangement.

10. The lead of claim 9, wherein both of the first and second sets of electrodes are arranged in a zigzag arrangement.

11. The lead of claim 1, wherein the distal end of the lead has a C-shaped transverse cross-sectional shape.

12. The lead of claim 1, wherein the distal end further comprises a single slit defined along at least a portion of the longitudinal length of the hollow interior region, wherein the hollow interior region is open along the single slit.

13. The lead of claim 1, wherein the hollow interior region is only open at a tip of the distal end of the lead.

14. The lead of claim 1, wherein the hollow interior region is open at least at a tip of the distal end of the lead.

15. The lead of claim 1, wherein at least one of the two or more of the electrodes disposed on the interior surface of the curved wall is facing another one of the two or more of the electrodes across the hollow interior region.

16. A method for stimulating patient brain tissue using the lead of claim 1, the method comprising:
    implanting the lead into a brain of a patient;
    disposing the proximal end of the lead into a connector, the connector configured and arranged for receiving the proximal end of the lead, the connector comprising a plurality of connective contacts that electrically couple to the plurality of terminals, the connector electrically coupled to a control module; and
    providing electrical signals from the control module to electrically stimulate patient tissue using at least one of the plurality of electrodes disposed on the distal end of the lead.

* * * * *